United States Patent [19]

Bonse et al.

[11] Patent Number: 5,229,284
[45] Date of Patent: Jul. 20, 1993

[54] ENZYME IMMOBILZATION ON A MACROPERMABLE AGGLOMERATE OF MICROPOROUS α-ALUMINUM OXIDE HYDROXIDE PARTICLES

[75] Inventors: Dirk Bonse, Lehrte-Arpke; Hubert Schindler, Uetze-Dollbergen; Hans-Joerg Mueller, Hanover, all of Fed. Rep. of Germany

[73] Assignee: Kali Chemie AG, Hanover, Fed. Rep. of Germany

[21] Appl. No.: 737,983

[22] Filed: Jul. 30, 1991

[30] Foreign Application Priority Data

Aug. 2, 1990 [DE] Fed. Rep. of Germany ....... 4024491

[51] Int. Cl.$^5$ .................. C12N 11/14; C12N 11/08; C12N 11/06
[52] U.S. Cl. .................. 435/176; 435/180; 435/181
[58] Field of Search .................. 435/176, 180, 181

[56] References Cited

U.S. PATENT DOCUMENTS

| | | | |
|---|---|---|---|
| 3,850,751 | 11/1974 | Messing | 435/176 |
| 4,229,536 | 10/1980 | De Filippi | 435/176 |
| 4,940,664 | 7/1990 | Muecke | 435/176 |

FOREIGN PATENT DOCUMENTS 216272 4/1987 European Pat. Off.
3228477 2/1984 Fed. Rep. of Germany.

*Primary Examiner*—David M. Naff
*Attorney, Agent, or Firm*—Foley & Lardner

[57] ABSTRACT

Enzymes are immboilized on an inorganic carrier which is a round, macropermeable agglomerate having a mulberry-type structure formed from spherical microporous α-aluminum oxide hydroxide particles. An organic polycondensate having free organic functional groups as enzyme binding sites penetrates the agglomerate. The α-aluminum oxide hydroxide particles of the agglomerate retain essentially their form prior to agglomeration. The polycondensate is prepared by reacting a polyimine with a dialdehyde or an epoxy compound. Preferably, the polyimine is polyethyleneimine, the dialdehyde is glutardialdehyde and the epoxy compound is an epoxyfunctional silicon resin, an aliphatic diepoxide or an aliphatic triepoxide. The agglomerate is prepared by granulating the α-aluminum oxide hydroxide particles in the presence of the polyimine to form the agglomerate having the polyimine dispersed throughout and then reacting the polyimine with the dialdehyde or the epoxy compound. A preferred enzyme is glucose isomerase.

14 Claims, No Drawings

ENZYME IMMOBILZATION ON A MACROPERMABLE AGGLOMERATE OF MICROPOROUS α-ALUMINUM OXIDE HYDROXIDE PARTICLES

BACKGROUND OF THE INVENTION

This invention relates to a process for preparing hydrolysis-stable, inorganic, enzyme carriers having organic enzyme binding sites and consisting of a round, macropermeable agglomerate of primary particles arranged to form a mulberry-type substructure, to the enzyme carriers prepared by the process of the invention, and to the carrier catalysts prepared by immobilizing enzymes on these carriers.

It is known in the art that carrier catalysts (i.e. carriers coated with enzyme) having high enzyme density can be prepared based on porous silicon dioxide or aluminum oxide carrier materials. These carrier catalysts exhibit a controlled material exchange and high productivity when used. Both the carrier materials of silicon dioxide and those of aluminum oxide cannot be compressed and can be prepared with defined pore structure and pore distribution as well as high pore volume.

Silicon dioxide as a carrier material is indeed an inexpensive and easily accessible starting material which can easily be prepared to have the properties required for enzyme carriers (for example porosity, grain fraction, bulk density etc) and which is also resistant to abrasion when subject to the hydrodynamic loads occurring in industrial practice. However, silicon dioxide carrier materials have the disadvantage that they are not stable to hydrolysis in the neutral to weakly alkaline pH range. This negative property leads in practice to problems when enzymes are immobilized on the silicon dioxide carrier material, the optimum activity of these enzymes requiring a carrier having neutral to weakly alkaline pH value. One example of such an enzyme is glucose isomerase which is used industrially immobilized on silicon dioxide carriers for partial conversion of glucose carrier into a mixture of glucose and fructose (high-fructose content syrup, HFS). The disadvantages of the silicon dioxide carrier material are clearly shown using this example of a carrier catalyst, since the silicon dioxide coated with enzyme is also clearly subjected to hydrolysis during the reaction of the glucose substrate (isomerization). The hydrolysis of the carrier results in a marked loss of carrier mass and an associated loss of enzyme, as a result of which the operating time of isomerization reactors may be considerably reduced. In extreme cases a blockage of the enzyme bed may even occur in the reactor with the result that the total residual activity of the carrier catalyst still present in the reactor (possibly up to 40% of the initial activity) may be lost.

Carriers made from aluminum oxide are stable toward hydrolysis, but the process of preparing them is complex. The starting material must be initially calcined at temperatures which are significantly above 1,000° C., then broken to obtain the required grain fraction and sieved. High losses of material occur during the breaking and sieving due to the chalky structure of the material, and the usable aluminum oxide carrier fraction obtained in this manner retains the undesirable property of chalking even after additional treatment measures and subsequent enzyme coating (carrier catalyst). This adverse property is disadvantageous for the use of such a carrier catalyst in industrial practice since abrasion, enzyme losses and reactor blockages occur under the hydrodynamic conditions which exist in the reactor.

SUMMARY OF THE INVENTION

It is the object of the invention to provide an enzyme carrier which overcomes the disadvantages of the prior art.

Another object of the invention is to provide an enzyme carrier composed of inorganic material which can be easily prepared from available materials.

An additional object of the invention is to provide an enzyme carrier which is resistant to hydrolysis and to chalking.

It is also an object of the invention to provide an enzyme carrier which can be produced without large losses of material.

Yet another object of the invention is to provide an enzyme carrier which is resistant to abrasion and enzyme losses and enables catalytic reactors to be operated for long periods of time.

A further object of the invention is to provide process for preparing an enzyme carrier of inorganic material which meets the foregoing objects.

Yet another object of the invention is to provide carrier-bound enzymes bound to an enzyme carrier which meets the foregoing objects.

These and other objects of the invention are achieved by providing a process for preparing an inorganic, enzyme carrier having organic enzyme binding sites and consisting of a round, macropermeable agglomerate of primary particles arranged to form a mulberry-type substructure, said process comprising:

a) granulating spherical primary particles of microporous α-aluminum oxide hydroxide of the formula AlO(OH) using an organic binder having cross-linkable reactive functional groups to form a mulberry-type substructure of aggregated primary particles in which the individuality of the primary particles is essentially retained;

b) reacting the binder dispersed throughout the agglomerate obtained in step a) with an organic hardener which reacts with the reactive functional groups of the binder to form a three-dimensional network of organic polycondensate which penetrates the mulberry-type substructure, whereby the shape and substructure of the agglomerate is strengthened; and c) retaining some of the reactive groups of the organic binder or organic hardener as free functional groups in the network-forming polycondensate available for subsequent enzyme bonding.

According to a further aspect of the invention, the objects are achieved by providing an inorganic, enzyme carrier having organic functional enzyme binding sites and consisting of a round, macropermeable agglomerate of primary particles which are arranged to form a mulberry-type substructure, wherein a) the mulberry-type substructure is formed from aggregated, spherical primary particles of microporous α-aluminum oxide hydroxide of the formula AlO(OH), and the individuality of the primary particles is essentially retained therein;

b) the shape and structure of the agglomerate is strengthened by a three-dimensional network consisting of an organic polycondensate which penetrates the mulberry-type substructure, and c) free organic functional groups are retained on the network-forming organic polycondensate as binding sites for enzymes.

DETAILED DESCRIPTION OF PREFERRED EMBODIMENTS

The invention relates to a process for preparing inorganic-based enzyme carriers having organic enzyme binding sites and consisting of a round, macropermeable agglomerate of primary particles arranged to form a mulberry-type substructure, the process being characterized in that a) spherical primary particles of microporous α-aluminum oxide hydroxide of the formula AlO(OH) are granulated using an organic binder having cross-linkable reactive functional groups to form a mulberry-type substructure of aggregated primary particles, so that the individuality of the primary particles is essentially retained therein, b) the shape and structure of the agglomerate obtained in a) is strengthened by reacting the binder interspersing the agglomerate with an organic hardener reacting with the reactive functional groups of the binder to form a three-dimensional network of organic polycondensate penetrating the mulberry-type substructure, so that c) some of the reactive groups of the organic binder and/or organic hardener are retained as free functional groups for enzyme bonding in the network-forming polycondensate.

A fine-grain, spherical, microporous α-aluminum oxide hydroxide of the formula AlO(OH) is used as primary particles for the enzyme carriers of the invention. It is an inexpensive, hydrolysis-stable starting material which is commercially available or can be prepared easily according to processes known per se. The α-aluminum oxide hydroxide is characterized by high chemical purity and generally has the following typical characteristics, but these are not to be understood as being limiting:

| Aluminum oxide content: | at least 75 wt. %, generally about 79 wt. %; |
|---|---|
| Grain size distribution: | <25 μm: maximum 40%; <45 μm: maximum 60%; >90 μm: maximum 20%; |
| Bulk density: | 0.45 to 0.65 g/ml; |
| Pore volume (PV): | at least 0.6 ml/g, generally about 0.75 ml/g; |
| Most frequent pore diameter (HPD): | 700 to 900 Angstroms; |
| Specific surface area: | at least 85 m$^2$/g, generally about 98 m$^2$/g. |

According to the above porosity data (PV, HPD), α-aluminum oxide hydroxide is very well suited to being a carrier material for immobilized enzymes. However, this material cannot be used as such as a technically usable enzyme carrier, since it has particle dimensions which are about one order of magnitude too small. The required grain size can also not be produced in acceptable yields because of the process (spray drying).

This deficiency of the particle dimensions being too small is remedied in accordance with the invention in that the α-AlO(OH) primary particle is granulated using an organic binder which has cross-linkable reactive functional groups to form a round agglomerate of technically suitable grain size, and the shape and the structure of the agglomerate is stabilized by reacting the organic binder with an organic hardener which may react with the reactive functional groups of the binder. The round agglomerates obtained consist of a cluster of α-AlO(OH) primary particles, which are placed next to one another only so tightly by the granulation and are joined to one another, so that the agglomerate remains macropermeable. The macropermeability of the agglomerate assures that the enzyme to be immobilized and its carrier will have unhindered access to the micropore system of the primary particles. Favorable enzyme uptake properties and a favorable material exchange are thus assured. The shape and structure of the agglomerate of primary particles arranged in mulberry fashion is stabilized by the polycondensate comprising the organic binder and the organic hardener used as cross-linking agent, so that an abrasion-resistant enzyme carrier is produced, the permeability of which is not impaired.

The result of the process of the invention is surprising, since it is not possible to prepare granules of α-AlO(OH), which are suitable as enzyme carriers, by conventional granulation of the α-AlO(OH) primary particles using, for example only water as moistening agent. Indeed, granules having the required particle dimensions, which also consist of a bed of primary particles, can also be produced by these conventional granulation methods, but these granules are not abrasion-resistant and not macropermeable. The abrasion resistance cannot be produced by subsequently applying the organic binder to the agglomerates obtained by granulation using only water. The interparticulate cavities of the mulberry-type substructure of the agglomerate are blocked by the abrasion of AlO(OH) which forms in the case of the granulation of the primary particles when using only water, as a result of which the macropermeability of the agglomerate is lost. If organic binder is subsequently applied to an agglomerate adhered in this manner, it may only penetrate the agglomerate to an insufficient extent. The shape and the structure of the agglomerate may be stabilized only to an insufficient extent by cross-linking of the organic binder with the organic hardener. Such agglomerates not according to the invention tend to break apart and are not abrasion-resistant.

Furthermore, in contrast to the carriers of the invention, these comparison agglomerates, which are not in accordance with the invention, also perform unfavorably as carrier catalysts with respect to enzyme uptake and material exchange, so that they are not suitable for technical use.

The advantages of the invention are achieved by using an organic binder in the granulation of primary particles, this binder having cross-linkable reactive functional groups, and by cross-linking the binder with an organic hardener which may react with the reactive functional groups of the binder. Not all functional groups of the binder and/or hardener are consumed by cross-linking the organic binder with the organic hardener, so that the network of the organic binder/hardener polycondensate serving to strengthen the enzyme carrier according to the invention advantageously makes free organic functional groups available for enzyme binding at the same time.

Polyimines are particularly advantageous as organic binders. Polyethyleneimine is preferably used as organic binder.

Dialdehydes or epoxy compounds are particularly advantageous as organic hardeners. A preferred dialdehyde used is glutardialdehyde; preferred epoxy compounds used are epoxy-functional silicon resins, for example from 3-glycidoxypropyltriethoxysilane and aliphatic diepoxides and triepoxides. Suitable epoxy-functional compounds are commercially available, for example, Epon 812 from Serva Co., Heidelberg, Germany, No. 21045. The epoxy-functional alkoxysilanes which can be used, for example 3-glycidoxypropyltriethoxysilane, are converted to the active trisilanol initially by hydrolysis under the influence of acid catalysts using water or water-containing organic solvents for use as hardeners. Hydrolysis proceeds rapidly, condensation of the primarily formed silanetriol (also acid-catalyzed) also taking place; but the epoxy function is retained. Stock solutions of epoxy-functional silicon resin obtained in this manner are diluted to the required concentration, for example using water or alcohol, and used for cross-linking the organic binder.

Primary, secondary and tertiary amino groups (from the binder) on the one hand, and aldehyde groups or epoxy groups (from the hardener) on the other hand, which do not participate in the cross-linking reaction between binder and hardener, are provided as enzyme binding sites by the organic binders or hardeners described above.

The granulation step of the process of the invention may be carried out in conventional granulation devices, such as for example mixers or rotary plates. Granulation may alternatively also be carried out as a spray granulation process in a fluidized bed.

For this, for example α-aluminum oxide hydroxide of the quality described above is initially placed in a suitable rotary plate and continuously sprayed over a short period, preferably about 5 to 20 minutes, with an aqueous solution of polyethyleneimine (PEI). Suitable α-aluminum hydroxide materials are commercially available, for example, "Pural" aluminum oxide hydrate from Messrs. Condea Chemie, Brunsbuetter, Germany. Aggregated macropermeable agglomerates of the α-AlO(OH) primary particles are thus obtained which are then classified according to grain size. The required agglomerate grain fraction (acceptable grain) is separated out, the remaining oversize grain fraction is comminuted and added again to the rotary plate together with the undersize grain fraction. The granulation process is continued with addition of fresh primary grain and further spraying with polyethyleneimine solution, until enough agglomerate is formed again and acceptable grain may be separated out. The process is continued until the required amount of acceptable grain is produced; the small residual amounts of oversize grain and undersize grain remaining from classifying the agglomerate may be temporarily stored and used as starting material for later production batches.

The process must not be carried out quasi-continuously, it is also possible to always start from fresh primary grain and to further process the side fractions thus collected at a later stage separately or together.

The amount of polyamine applied to the primary particles may be controlled by varying the concentration of sprayed polyimine solution, the spraying time and the throughput during the spraying. In a preferred embodiment of the process of the invention, an aqueous solution of the polyimine, preferably polyethyleneimine, in a concentration of 5 to 15 wt.% is used with application times of 5 to 20 minutes. Aqueous solutions of polyimine having a concentration of about 10 wt.% of polyimine, which are advantageously used with spraying times of about 10 minutes, are particularly preferred. The throughput of polyimine solution is preferably adjusted in the process so that approximately 0.5 kg of polyimine solution are applied per 1 kg of α-aluminum oxide hydroxide. Enzyme carriers prepared according to the invention in this manner have polyimine contents of 3 to 7 wt. %, preferably 4 to 6 wt. % (relative to the total weight of the enzyme carrier) in the classified acceptable grain fraction.

The acceptable grain fraction of the agglomerate produced is advantageously further rolled in the rotary plate while spraying further with polyethyleneimine solution for a short period, preferably about 3 to 5 minutes.

The acceptable grain produced is then dried at temperatures of about 60° C. to a residual moisture content $\leq 5$ wt. %. Any suitable continuous or discontinuous drying process per se may be used for this. The shape and structure of the dried, round agglomerates of α-AlO(OH) primary particles, which are arranged to form a mulberry-type, macropermeable substructure, are then stabilized by contacting with amine-reactive cross-linking agents (hardeners). The agglomerate material is thus added, for example, to a phosphate buffer solution containing glutardialdehyde or is soaked with a solution of epoxy-functional silicon resins or aliphatic diepoxides or triepoxides. This process step is not critical. After sufficient reaction time, the agglomerate stabilized by cross-linking is washed to remove residues of the cross-linking agent.

The finished enzyme carrier is then present and can subsequently be used for enzyme fixation, optionally moist or also dry.

The invention also relates to enzyme carriers which may be prepared by the processes described above. These objects of the invention are inorganic-based enzyme carriers having organic functional enzyme binding sites and consisting of a round, macropermeable agglomerate of primary particles which are arranged to form a mulberry-type substructure, this enzyme carrier being characterized in that a) the mulberry-type substructure is formed from aggregated, spherical primary particles of microporous α-aluminum oxide hydroxide of the formula AlO(OH) and the individuality of the primary particles is essentially retained therein, b) the shape and structure of the agglomerate is strengthened by a three-dimensional network penetrating the mulberry-type substructure and consisting of an organic polycondensate, and c) the network-forming organic polycondensate still has free organic functional groups as binding sites for enzymes.

The invention also relates to carrier-bound enzymes (carrier catalysts) which are characterized in that they are bound to the enzyme carrier according to the invention described above. A particularly preferred use of the enzyme carrier of the invention is to immobilize glucose isomerase. This application makes full use of the advantages of the enzyme carrier of the invention.

The active components, that is enzymes such as glucose isomerase, may be applied directly to the enzyme carriers according to the invention. Pretreatment of the carrier for producing enzyme binding sites is no longer necessary, since an adequate number of binding sites required for immobilization are already provided during the preparation of the enzyme carrier according to the invention by means of the network-forming organic polycondensate, on the one hand, for example by unreacted primary as well as secondary and tertiary amino groups from the binder, and on the other hand, for example by unreacted aldehyde or epoxy groups from the hardener. The carriers are therefore simply contacted with a conventional liquid enzyme preparation so that the enzyme is fixed at the aforementioned binding sites. The enzyme fixed on the enzyme carrier can then also be subjected to cross-linking in a known manner.

Novel enzyme carriers, which can be prepared very simply and inexpensively, are advantageously made available by means of the invention. The enzyme carriers according to the invention have a round shape which yields advantageous flow characteristics, they are stable to hydrolysis, abrasion-resistant and yet macropermeable, which assures favorable material exchange. The enzyme carrier of the invention is thus distinguished from the broken $SiO_2$ carriers (Splitt) of the prior art which are not stable toward hydrolysis and which have a shape which produces disadvantageous flow characteristics. The enzyme carriers of the invention are also distinguished from the broken $Al_2O_3$ carriers (Splitt) of the prior art, since $Al_2O_3$ carriers can only be produced with high losses in yield due to the chalky structure of the porous aluminum oxide. $Al_2O_3$ carriers also are not abrasion-resistant and exhibit disadvantageous flow characteristics. The advantages of the enzyme carriers of the invention are also fully exploited in the carrier catalysts prepared therefrom.

The following examples serve to illustrate the invention in further detail without limiting its scope.

I. Preparation of carriers according to the invention

Spherical α-aluminum oxide hydroxide of the formula AlO(OH) prepared by spray-drying and having the following typical characteristics are used for subsequent preparation of the carriers of the invention:

| | |
|---|---|
| Aluminum oxide content: | 79 wt. % |
| Grain size distribution: | <25 μm: 12.9% |
| | <45 μm: 57.6% |
| | <90 μm: 23.5% |
| | >90 μm: 6.0% |
| Bulk weight: | 0.52 g/ml |
| Pore volume (PV): | 0.75 ml/g |
| Most frequent pore diameter (HPD): | 742 Angstroms |
| Specific surface area: | 98 m²/g |

Carrier No. 1

3 kg of aluminum oxide hydroxide of the formula AlO(OH) were initially placed in a rotary plate and sprayed with a 9.7 wt. % strength aqueous polyethyleneimine solution over a period of 12 minutes. An agglomerate having particle diameters of 0.3 to 0.6 mm is obtained as the acceptable grain fraction. The polyethyleneimine content of the acceptable grain was 5.9 wt. % (C/N analysis). The agglomerate was then dried at about 60° C. to a residual moisture content ≦5 wt. %. The dried material was then cross-linked using a 2.5 wt. % strength solution of glutardialdehyde in 0.05 molar phosphate buffer with a pH value of 6.0 (3 ml solution/g carrier) over a period of 1 hour. The resulting cross-linked agglomerate was washed free of glutardialdehyde residues and dried at about 60° C.

Carrier No. 2

The preparation was carried out as for carrier No. 1, except the spraying time was 8 minutes and agglomerates having polyethyleneimine contents of 4.1 wt. % (C/N analysis) were obtained.

Carrier No. 3

α-Aluminum oxide hydroxide was initially sprayed over a period of 14 minutes using polyethyleneimine solution in analogous manner to the preparation of carrier No. 1. Agglomerates having a polyethyleneimine content of 6.8 wt. % (C/N analysis) were obtained. The resulting agglomerate was dried at 60° C., and the dried material was then cross-linked by soaking with an ethanol solution of epoxy-functional silicon resin (75 mg resin/g carrier). The carrier stabilized by cross-linking was then dried at 60° C. and then at 110° C.

The ethanol solution of epoxy-functional silicon resin used for cross-linking was prepared as follows: 30 ml of water (which contains 300 mg of 60% strength perchloric acid per liter) were added to 70 ml of 3-glycidoxypropyltriethoxysilane, and the resulting mixture was stirred vigorously for 30 minutes. After standing for 1 hour, a test was made to see whether all the ethoxysilane has been completely hydrolyzed to the silanetriol (no clouding) by diluting a small amount to ten times the volume using water. The homogeneous mixture was then diluted using ethanol (90% strength) to 7.5 vol.% active ingredient content, and the carrier was soaked in the solution (1 ml solution per gram carrier).

Carrier No. 4

α-Aluminum oxide hydroxide was initially granulated to form an agglomerate using polyethyleneimine solution in a manner analogous to the preparation of carrier No. 1. The agglomerate was then cross-linked by soaking with a solution of aliphatic diepoxides and triepoxides in dioxane (70 mg epoxy compound per gram carrier). The reaction was allowed to proceed for 24 hours at 20° C. and for 1 hour at 90° C. The agglomerate stabilized by cross-linking was then washed with acetone until it was free of epoxy groups and dioxane. It was thereafter dried at 60° C. and then at 110° C.

Carrier No. 5

2 kg of α-aluminum oxide hydroxide of the formula AlO(OH) were granulated in a fluidized bed spray granulator using a 4.25 wt. % strength aqueous polyethyleneimine solution. The polyethyleneimine content of the resulting agglomerate was 5.8 wt. % (C/N analysis). The agglomerate was stabilized by cross-linking using glutardialdehyde in a manner analogous to the preparation of carrier No. 1.

II. Preparation of comparative carriers not according to the invention

Comparative carrier No. V1

Spherical α-aluminum oxide hydroxide of the formula AlO(OH) was initially granulated to form an agglomerate in a manner analogous to carrier No. 1, except that instead of aqueous polyethyleneimine solution, only water was used for moistening during granulation. Subsequently, the dried acceptable grain fraction which was obtained was soaked in 5 wt. % of polyethyleneimine from aqueous solution, and the material was cross-linked using glutardialdehyde in the same manner as carrier No. 1.

Comparative carrier No. V2

Extrusions of α-aluminum oxide hydroxide of the formula AlO(OH) having a diameter of 0.75 mm were soaked with 5 wt. % of polyethyleneimine from aqueous solution. Cross-linking was carried out a) using glutardialdehyde as in the same manner as carrier No. 1;

b) using epoxy-functional silicon resin in the same manner as carrier No. 3; and c) using aliphatic diepoxides and triepoxides in the same manner as carrier No. 4.

Comparative carrier No. V3

Pre-prepared granules of α-aluminum oxide hydroxide having particle diameters of 0.5 to 1 mm obtained from the manufacturer (Messrs. Condea Chemie) were soaked with 4 wt. % of polyethyleneimine from aqueous solution. Cross-linking was carried out using glutardialdehyde in the same manner as carrier No. 1.

III. Preparation of carrier catalysts

The carriers of the invention prepared as described in Section I above, and the comparative carriers prepared as described in Section II above, were equilibrated using 0.05 molar sodium acetate buffer (pH 5.7). After removing the excess buffer, 14,000 U of glucose isomerase (from *Streptomyces rubiginosus*) in a total liquid volume of 3 ml of a 0.05 molar sodium acetate buffer were added per gram of carrier (1 U is defined as the amount of enzyme which converts glucose to fructose under initial reaction conditions at a rate of mg/ml.hour; 2 molar glucose carrier in 0.1 molar maleate buffer (pH 7) having 5 moles of $Mg^{++}$ and 0.125 mmoles of $Co^{++}$, 60° C.). The mixtures were allowed to stand with occasional agitation for 20 hours and the pH value was maintained at ≦pH 6.5. The carriers were then washed using 0.05 molar sodium acetate buffer to remove any enzyme which may not have bonded. The excess washing buffer was removed by suction, and then 3 ml of a 2.5 wt. % strength solution of GDA in 0.05 molar sodium acetate buffer were added per gram of carrier. The mixture was occasionally agitated over the course of 30 minutes, the GDA solution was then removed by suction, and the material was washed using 0.05 molar sodium acetate buffer and then using distilled water to remove excess GDA. After removing excess moisture by suction, 2 ml of a 4 wt. % strength aqueous solution of polyethyleneimine, which was set at pH 5.0 using sulfuric acid, were added per gram of carrier. After standing for 20 hours, during which there was occasional agitation, the excess polyethyleneimine solution was separated, and the catalysts were washed using water. After exchanging the washing water for 0.05 molar phosphate buffer (pH 6) containing preservative agents, the carrier catalysts could be stored.

The enzyme uptake of the carrier catalysts prepared in this manner was determined from the difference in the activities of the immobilization mixture before and after coating the carrier with enzyme. The enzyme uptake was typically between 96 and 100% of the amount of enzyme available.

The properties of the carrier catalysts prepared according to the invention are compiled in Table I, and the properties of the comparative carrier catalysts are compiles in Table II.

TABLE I

| | Carriers and carrier catalysts of the invention | | | | | |
|---|---|---|---|---|---|---|
| Carrier No. | Enzyme uptake (U/ml cat) | SV (ml/ml · h) | Test time (h) | Residual activity (%) | Productivity $t_{HFS}/l$ cat | Catalyst residual mass (%) |
| I. 1 | 7824 | 7.3 | 2250 | 50 | | |
| I. 2 | 8598 | 7.3 | 5000 | 20 | 9.6 | 97 |
| | | | 2550 | 50 | | |
| I. 3 | 7220 | 6.3 | 5240 | 20 | 9.7 | 98 |
| | | | 2150 | 50 | | |
| I. 4 | 7268 | 6.3 | 4400 | 20 | 7.5 | 98 |
| | | | 2950 | 50 | | |
| I. 5 | 7774 | 6.7 | 5081 | 20 | 9.2 | 97 |
| | | | Short time test only | 50 | | 100 |
| Comparison* | 7223 | 6.3 | 1650 | 50 | | |
| | | | 2758** | 29 | 5.2 | 12.5 |

*porous $SiO_2$ carrier of the state of the art
**reactor blocked because of carrier dissolving
cat = catalyst
SV = space velocity

TABLE II

| Comparative material not according to the invention | | |
|---|---|---|
| Carrier No. | Enzyme uptake (U/ml · cat) | Space velocity (SV) (ml/ml · h) |
| II. V1 | 2850 | 2.3 |
| II. V2 a | 3205 | 2.8 |
| | 3310 | 2.9 |
| | 3250 | 2.8 |
| II. V3 | 3740 | 3.4 |

IV. Properties of Carrier Catalysts of the Invention Compared to Carrier Catalysts Not of the Invention The suitability as carrier catalyst for glucose isomerase (enzyme uptake, initial space velocity, productivity) and the abrasion-resistance were used to judge the quality of the enzyme carriers of the invention.

a) Abrasion resistance

The abrasion resistance was tested in a stress test, which simulates hydrodynamic loads to which the material may be subjected under practical conditions. One gram of carrier or carrier catalyst together with 4 grams of water were added to a cylindrical vessel (diameter 20 mm) for this test and placed under stress on a whirl mixer at full power (1,400 minute.: under load). Carrier material which after two minutes showed no clouding in the supernatant of the suspension was classified as abrasion-resistant. The enzyme carriers or carrier catalysts prepared according to the invention proved to be abrasion-resistant without exception.

b) Isomerization

The abrasion-resistant carrier catalysts of the invention and the comparative preparations not of the invention were investigated for their efficiency under isomerization conditions which correspond to the conditions in practice. For this the carrier catalysts were incorporated in a temperature-controlled column reactor and preheated carrier was passed through the carrier catalyst bed using a metering pump. The throughput of the carrier solution was set so that a degree of isomerization of 46.5% was reached and maintained over the entire duration of the test. The reaction temperature was 60° C. The carrier used had the following composition:

45 wt. % glucose in aqueous solution,
120 ppm Mg (II) as $MgSO_4$,
300 ppm $SO_2$ as $Na_2SO_3$,
pH value 7.5.

c) Results

The results are compiled in Tables I and II. The enzyme uptake is given in U/ml of catalyst, 1 U being defined as the amount of enzyme which converts glucose to fructose under initial reaction conditions at a rate of 1 mg/ml.hour (2 molar glucose carrier in 0.1 molar maleate buffer pH 7 having 5 mmoles of $Mg^{++}$, 0.125 mmoles of $Co^{++}$, 60° C.).

The initial space velocity (SV=ml of carrier/ml of catalyst.hour) is given as a measure of the carrier catalyst activity.

In as far as the productivity was tested in the sustained time test, it is given in conjunction with the residual activity which is still present in $t_{HFS}$(TS)/liter of carrier catalyst.

At the end of the test the catalyst packing was removed in each case, washed with water until is was free of sugar, dried, and the residual mass was determined by weighing.

Table I

The results in Table I show that the enzyme carriers of the invention are outstandingly suitable for preparing carrier catalysts. Equally high values were reached with respect to enzyme uptake and enzyme efficiency in the immobilized state compared to the porous silicon dioxide carrier of the prior art given as a comparison. The carrier material of the invention is clearly superior with regard to operating life (compare $t_{50\%}$, $t_{20\%}$) and productivity, since it is stable toward hydrolysis in the glucose carrier and is not gradually dissolved (see catalyst residual masses) like the silicon dioxide carrier of the prior art.

Comparable, in some cases even higher half-life values of up to about $t_{50\%}=3,000$ hours were achieved using the enzyme carriers of the invention compared to aluminum oxide carriers of the prior art having half-life values of about $t_{50\%}=2,500$ hours. However, compared to the aluminum oxide carriers of the prior art, the enzyme carriers of the invention have the additional advantage that they may be produced at considerably lower cost (50% of the cost of an aluminum oxide carrier), and they do not have the disadvantage of always chalking under the hydrodynamic stress to which they are subjected when used.

Table II

The comparative carrier of α-aluminum oxide hydroxide prepared under II or obtained already refined from the manufacturer are unfavorably blocked in respect of enzyme uptake, achievable space velocity and abrasion behavior (not abrasion-resistant in the stress test) compared with carriers of the invention, so that they were not tested in the sustained time test (productivity) because they are not technically suitable.

The low enzyme uptakes and low space velocities show that the comparative preparations do not have the adequate macropermeable substructures which ensure the required material exchange during enzyme coating and substrate conversion.

Microscopic inspection confirmed that a cluster of primary grains of α-aluminum oxide hydroxide is indeed also present in the comparative carrier II. No V1, but the particles in this cluster are substantially adhered to each other by abrasion which arises during spray granulation using only water (instead of aqueous polyethyleneimine solution), so that it loses its permeability. As a result, the polyethyleneimine, which in this case is applied only after granulation of the primary grains, cannot penetrate the cluster adequately. Thus, after cross-linking the shape and structure of the granules are not adequately stabilized as evidenced by the wear exhibited in the stress test.

The comparison carriers II. No. V2 and II. No. V3 (which are based on preformed, commercially available α-aluminum oxide hydroxide carriers) did not show any substructure of primary grains upon microscopic inspection. Apparently, during the conventional forming processes (pressing, granulation) to which they were subjected, the macroscopic substructure was completely destroyed. The comments made above with respect to comparison carrier II. No. V1 apply similarly to the efficacy of the organic binder and the cross-linking agent (polyethyleneimine/glutardialdehyde etc.) which in this case also were first applied to the completed formed bodies. The comparison carriers II. No. V2 and II. No. V3 are abraded in the stress test.

Overall, the enzyme carriers according to the invention are thus decisively superior to the comparison materials of the prior art. The enzyme carriers of the present invention have the following advantages: they are macropermeable (which yields favorable material exchange); nevertheless they are abrasion resistant; they have a round (substantially spherical) shape so that they exhibit favorable flow properties compared to "Splitt", they are stable toward hydrolysis under operating conditions, and additionally they are very inexpensive to produce.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A process for preparing an inorganic, enzyme carrier having organic enzyme binding sites and consisting of a round, macropermeable agglomerate of spherical particles arranged to form a mulberry structure, said process comprising:
   a) granulating spherical particles of microporous α-aluminum oxide hydroxide of the formula AlO(OH) using a polyimine to form an agglomerate having mulberry structure of aggregated spherical particles in which the individuality of the spherical particles is essentially retained and in which the polyimine is dispersed throughout the agglomerate;

b) reacting the polyimine dispersed throughout the agglomerate obtained in step a) with an organic hardener selected from the group consisting of dialdehydes and epoxy compounds which reacts with the polyimine to form a three-dimensional network of organic polycondensate which penetrates the mulberry structure of the agglomerate, whereby the shape and structure of the agglomerate is strengthened; and c) retaining some reactive groups of the polyimine or organic hardener as free functional groups in the network-forming polycondensate available for subsequent enzyme bonding.

2. A process according to claim 1, wherein said polyimine is polyethyleneimine.

3. A process according to claim 1, wherein said hardener is glutardialdehyde.

4. A process according to claim 1, wherein said hardener is selected from the group consisting of epoxy-functional silicon resins, aliphatic diepoxides and aliphatic triepoxides.

5. A process according to claim 1, wherein said polyimine used in the granulating step a) is an aqueous solution.

6. A process according to claim 5, wherein the polyimine used in the granulating step a) is in the form of a 5 to 15 wt. % strength aqueous polyimine solution.

7. A process according to claim 6, wherein approximately 0.5 kg of said aqueous polyimine solution is used in step a) per kilogram of α-aluminum oxide hydroxide particles.

8. A process according to claim 5, wherein said spherical particles are granulated over a period of 5 to 20 minutes while being sprayed with said aqueous polyimine solution.

9. A process according to claim 5, wherein the agglomerate obtained in the granulation step a) is rolled over a period of approximately 3 to 5 minutes while continuing spraying with said aqueous polyimine solution.

10. A process according to claim 1, wherein the agglomerates of α-aluminum oxide hydroxide prepared int eh granulating step a) contain from 3 to 7 wt. % polyimine.

11. A process according to claim 10, wherein the agglomerates of α-aluminum oxide hydroxide prepared in the granulating step a) contain from 4 to 6 wt. % polyimine.

12. An organic, enzyme carrier having organic functional enzyme binding sits and consisting of a round, macropermeable agglomerate of spherical particles which are arranged to form a mulberry structure, wherein the carrier has:

a) an agglomerate of aggregated, spherical particles of microporous α-aluminum oxide hydroxide of the formula AlO(OH) having said mulberry structure whereby the individuality of the spherical particles is essentially retained;

b) a three-dimensional network consisting of an organic polycondensate of a polyimine and a dialdehyde or an epoxy compound, which penetrates the mulberry structure of the agglomerate, and c) free organic functional groups present on the organic polycondensate as binding sites for enzymes.

13. A carrier-bound enzyme comprising an enzyme immobilized on an inorganic enzyme carrier having organic functional enzyme binding sites and consisting of a round, macropermeable agglomerate of spherical particles which are arranged to form a mulberry structure, wherein the carrier has:

a) an agglomerate of aggregated, spherical particles of microporous α-aluminum oxide hydroxide of the formula AlO(OH) having said mulberry structure, wherein the individuality of the spherical particles is essentially retained;

b) a three-dimensional network consisting of an organic polycondensate of a polyimine and a dialdehyde or an epoxy compound which penetrates the mulberry structure of the agglomerate, and c) free organic functional groups present on the organic polycondensate as binding sites for enzymes.

14. A carrier-bound enzyme according to claim 13, wherein said enzyme is glucose isomerase.

* * * * *